(12) United States Patent
Nakayama

(10) Patent No.: US 11,369,345 B2
(45) Date of Patent: Jun. 28, 2022

(54) METHOD FOR PRODUCING MEMS TRANSDUCER, MEMS TRANSDUCER, ULTRASOUND PROBE, AND ULTRASOUND DIAGNOSTIC APPARATUS

(71) Applicant: KONICA MINOLTA INC., Chiyoda-ku (JP)

(72) Inventor: Yuta Nakayama, Chiba (JP)

(73) Assignee: KONICA MINOLTA, INC., Tokyo (JP)

( * ) Notice: Subject to any disclaimer, the term of this patent is extended or adjusted under 35 U.S.C. 154(b) by 1031 days.

(21) Appl. No.: 16/024,984

(22) Filed: Jul. 2, 2018

(65) Prior Publication Data

US 2019/0008479 A1 Jan. 10, 2019

(30) Foreign Application Priority Data

Jul. 7, 2017 (JP) .................. 2017-133827

(51) Int. Cl.
*H01L 41/312* (2013.01)
*A61B 8/00* (2006.01)
(Continued)

(52) U.S. Cl.
CPC .......... *A61B 8/4494* (2013.01); *A61B 8/4444* (2013.01); *A61B 8/5207* (2013.01); *B06B 1/0215* (2013.01); *B06B 1/06* (2013.01); *B06B 1/0622* (2013.01); *B06B 1/0666* (2013.01); *B81B 7/007* (2013.01); *B81C 1/00301* (2013.01); *B81C 3/004* (2013.01); *B81C 3/005* (2013.01); *G01N 29/245* (2013.01);
(Continued)

(58) Field of Classification Search
CPC ............... H01L 41/042; H01L 41/0475; H01L 41/0825; H01L 41/1876; H01L 41/312; H01L 2223/54426; H01L 2223/54466; B81B 2201/0271; B81B 2207/012; B81B 2207/015; B81B 2207/096; B81C 2203/03; B81C 2203/05; B81C 2203/051; B81C 2203/057; B81C 2203/0792; A61B 8/4494; A61B 8/4444; A61B 8/5207; Y10T 29/42
USPC ...................................................... 29/25.35
See application file for complete search history.

(56) References Cited

U.S. PATENT DOCUMENTS

2011/0086443 A1 4/2011 Kobayashi et al.
2016/0027991 A1* 1/2016 Suzuki ................ A61B 8/5207
600/447

FOREIGN PATENT DOCUMENTS

JP 2004-363746 12/2004
JP 2006-202918 8/2006
(Continued)

OTHER PUBLICATIONS

Office Action dated Dec. 1, 2020 issued in Japanese Patent Application No. 2017-133827.

*Primary Examiner* — Peter Dungba Vo
*Assistant Examiner* — Azm A Parvez
(74) *Attorney, Agent, or Firm* — Cozen O'Connor

(57) ABSTRACT

Substrate is produced by using a MEMS technique to form multiple diaphragms in a substrate by forming piezoelectric material layer on one surface of the substrate and thereafter by forming openings in the substrate from the other surface of the substrate; substrate and substrate on which signal detection circuit is formed are aligned to each other using at least one of multiple diaphragms as alignment diaphragm; and substrate and substrate are bonded together.

6 Claims, 10 Drawing Sheets

(51) Int. Cl.
*H01L 23/544* (2006.01)
*B81C 3/00* (2006.01)
*B06B 1/06* (2006.01)
*A61B 8/08* (2006.01)
*B06B 1/02* (2006.01)
*B81B 7/00* (2006.01)
*B81C 1/00* (2006.01)
*G01N 29/24* (2006.01)
*H01L 41/04* (2006.01)
*H01L 41/047* (2006.01)
*H01L 41/08* (2006.01)
*H01L 41/187* (2006.01)

(52) U.S. Cl.
CPC .......... *H01L 23/544* (2013.01); *H01L 41/042* (2013.01); *H01L 41/0475* (2013.01); *H01L 41/0825* (2013.01); *H01L 41/1876* (2013.01); *H01L 41/312* (2013.01); *A61B 2562/028* (2013.01); *B06B 2201/76* (2013.01); *B81B 2201/0271* (2013.01); *B81B 2203/0127* (2013.01); *B81B 2207/012* (2013.01); *B81B 2207/015* (2013.01); *B81B 2207/096* (2013.01); *B81C 2203/03* (2013.01); *B81C 2203/05* (2013.01); *B81C 2203/051* (2013.01); *B81C 2203/057* (2013.01); *B81C 2203/0792* (2013.01); *H01L 2223/54426* (2013.01); *H01L 2223/54466* (2013.01); *Y10T 29/42* (2015.01)

(56) References Cited

FOREIGN PATENT DOCUMENTS

| | | |
|---|---|---|
| JP | 2007-276157 | 10/2007 |
| JP | 2007276157 A * | 10/2007 |
| JP | 5108100 | 12/2012 |
| JP | 2013-539254 | 10/2013 |
| JP | 5450396 | 3/2014 |
| JP | 2016-181840 | 10/2016 |
| WO | WO 2008/148736 | 12/2008 |

* cited by examiner

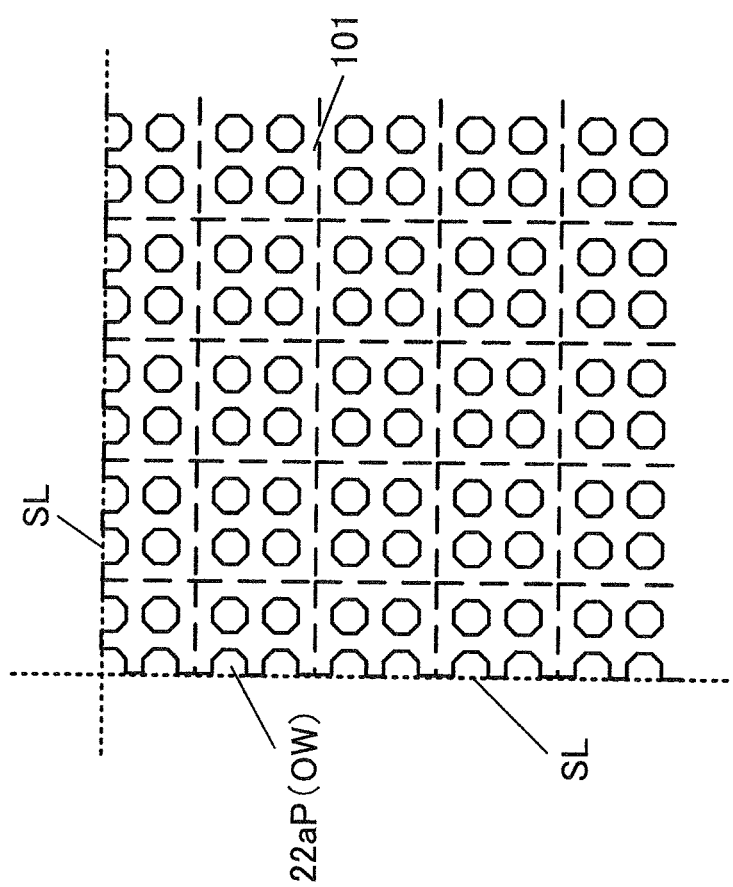

METHOD FOR PRODUCING MEMS TRANSDUCER, MEMS TRANSDUCER, ULTRASOUND PROBE, AND ULTRASOUND DIAGNOSTIC APPARATUS

CROSS REFERENCE TO RELATED APPLICATIONS

The entire disclosure of Japanese Patent Application No. 2017-133827, filed on Jul. 7, 2017, is incorporated herein by reference in its entirety.

BACKGROUND

Technological Field

The present invention relates to a method for producing a MEMS transducer used for transmission/reception of ultrasonic waves, a MEMS transducer, an ultrasound probe, and an ultrasound diagnostic apparatus.

Description of Related Art

Micro electro mechanical system (MEMS) devices produced by MEMS techniques using semiconductor manufacturing techniques have spread recently. The MEMS devices are used for sensors, transducers, and the like.

Examples of those of the transducers which are configured to generate ultrasonic waves (ultrasound transducers) include a piezoelectric micromachined ultrasonic transducer (pMUT). The pMUT transmits/receives ultrasonic waves by causing vibration of a diaphragm (movable film) in the same manner as a drum. The diaphragm has a unimorph structure in which a piezoelectric thin film (actuator layer) such as PTZ is formed on a substrate (base material layer) such as a silicon substrate or the like.

As compared, for example, with piezoelectric elements divided by dicing or the like of a bulk PTZ, the pMUT has various characteristics as follows: a frequency bandwidth can be wider; further micromachining is possible, so that high-resolution can be expected; the pMUT is suitable for forming a two-dimensional array of piezoelectric elements for generating three-dimensional images; miniaturization and thickness reduction is possible; and the like.

Examples of semiconductor manufacturing methods using MEMS techniques include techniques disclosed in Japanese Patent No. 5108100, Japanese Patent No. 5450396, and Japanese Patent Application Laid-Open No. 2006-202918, for example.

Such a pMUT is produced by bonding together a substrate (MEMS substrate) in which diaphragms are formed, another substrate (electronic circuit substrate) on which a signal detection circuit (e.g., CMOS circuit) adapted to detect transmission/reception signals for transmission/reception of ultrasonic waves at the diaphragms is formed, interposer, and connecting wiring such as a flexible wiring board or the like.

In this respect, when it is attempted to produce the pMUT by forming the MEMS substrate and electronic substrate at the same time (i.e., by forming the MEMS substrate on the electronic circuit substrate on which the signal detection circuit has been formed, for example), the following disadvantages are caused. That is, high temperature annealing is required in order to deposit a preferable piezoelectric thin film (for example, PZT) on the MEMS substrate, so that the signal detection circuit may be damaged by the high temperature. Additionally, when the MEMS substrate is formed on the signal detection circuit of the electronic circuit substrate, the signal detection circuit of the same size as the MEMS substrate needs to be prepared and this necessity causes a disadvantage in terms of yield of the signal detection circuit. Accordingly, it is desirable for the MEMS substrate and the electronic circuit substrate to be manufactured individually and then bonded together.

When the MEMS substrate and the electronic circuit substrate are manufactured individually and then bonded together, highly accurate alignment in bonding is required for achieving a higher-definition and higher-resolution ultrasound diagnostic apparatus. However, for achieving highly accurate alignment, dedicated equipment for highly mechanically accurate alignment and/or additional machining for alignment are required, which cost greatly. Moreover, there has been a problem of low accuracy due to inability to directly observe connected surfaces when bonding together the MEMS substrate and the electronic circuit substrate. Thus, in cases where high-density and multi-pin connection is required as in the case of ultrasonic transducers, there has been a risk of a connection error being caused.

Additionally, there has been a demand for different ultrasound probes (e.g., linear type, convex type, sector type, and the like) to be properly used, and similarly, there also has been a demand for multiple MEMS substrates of different sizes and shapes to be prepared in advance and to be properly used according to observation targets during ultrasonic diagnosis using an ultrasound diagnostic apparatus. In contrast, as for the electronic circuit substrate, it is preferable in view of the cost that the same circuit can possibly be used. For the reasons as stated above, it is desirable for the MEMS substrate to mainly include alignment means.

Thus, there is a demand for a technique making it possible to connect the MEMS substrate and the electronic circuit substrate with high accuracy and at low cost.

SUMMARY

Objects of the present invention are to provide a method for producing of a MEMS transducer, in which a MEMS substrate and an electronic circuit substrate can be connected with high accuracy and at low cost, a MEMS transducer, an ultrasound probe, and an ultrasound diagnostic apparatus.

In order to achieve at least one of the aforementioned objects, the method for producing of the MEMS transducer, in which one aspect of the present invention is reflected, includes: producing a MEMS substrate by using a MEMS technique to form a plurality of diaphragms in a substrate, the plurality of diaphragms being formed by forming a piezoelectric material layer on one surface of the substrate and thereafter by forming openings in the substrate from the other surface of the substrate; performing alignment between the MEMS substrate and an electronic circuit substrate by using at least one of the plurality of diaphragms as an alignment diaphragm; and bonding together the MEMS substrate and the electronic circuit substrate.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIG. 10 is an explanatory view for explaining a case where the alignment diaphragm is provided on one of scribe lines SL.

DETAILED DESCRIPTION OF EMBODIMENTS

Hereinafter, one or more embodiments of the present invention will be described with reference to the drawings. However, the scope of the invention is not limited to the disclosed embodiments.

Figure 1:
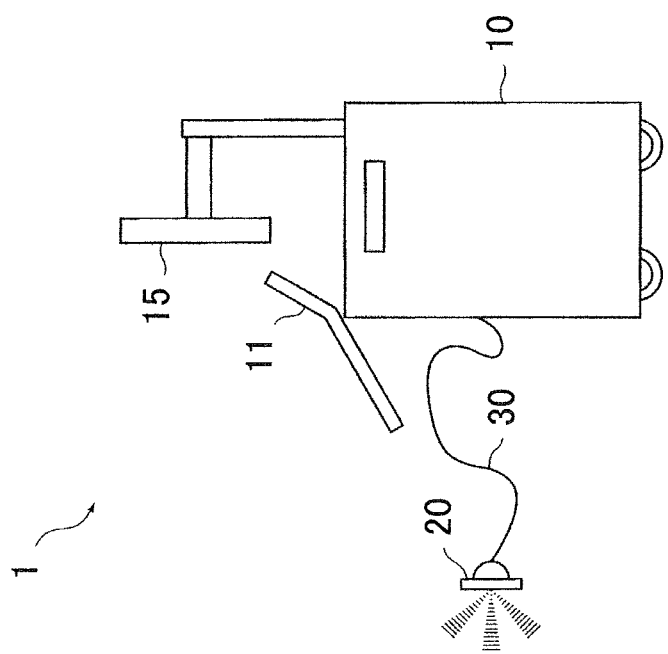
FIG. 1 illustrates a configuration in external appearance of an ultrasound diagnostic apparatus including an ultrasonic transducer.
Figure 2:
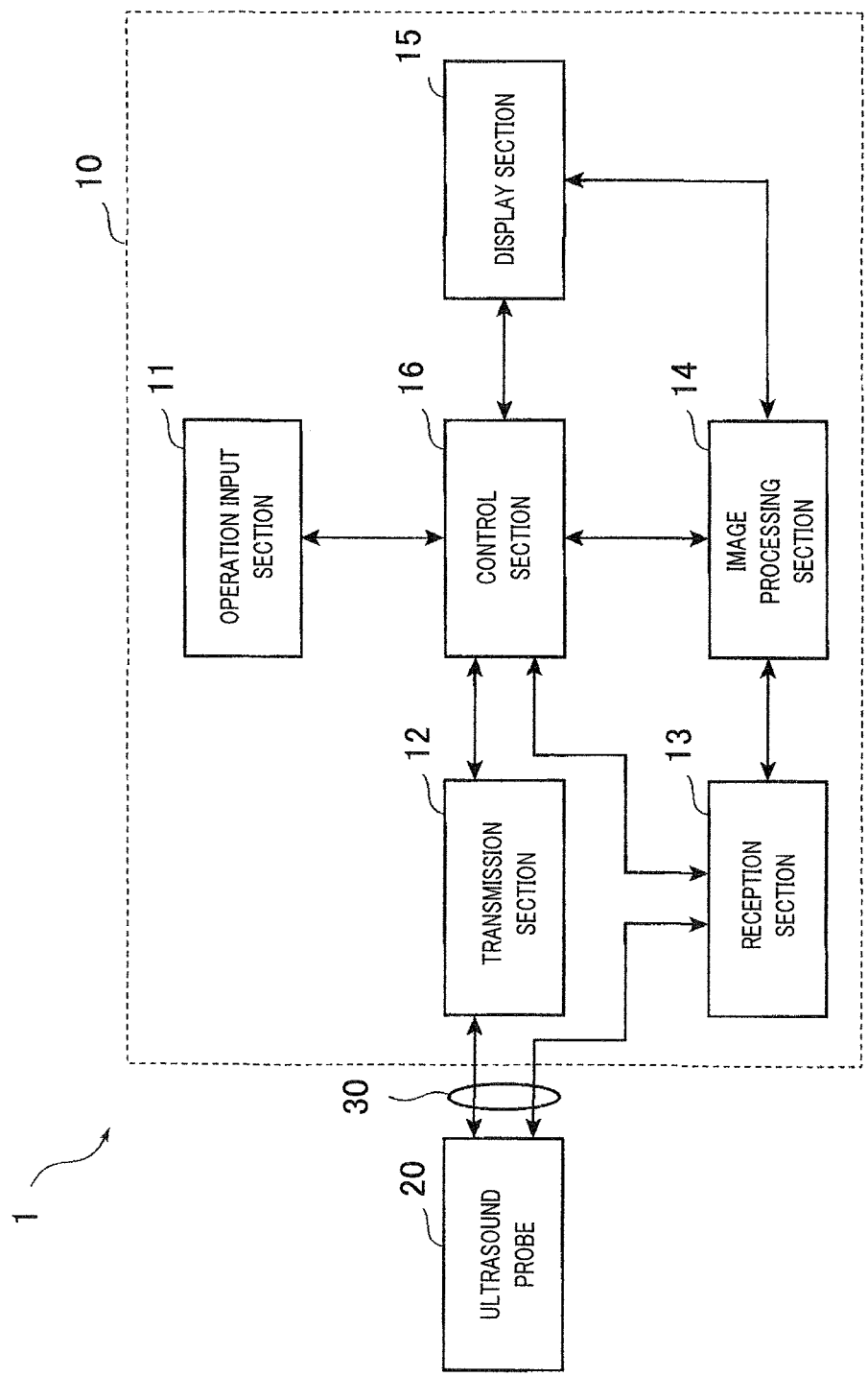
FIG. 2 is a block diagram illustrating an electrical configuration example of the ultrasound diagnostic apparatus.

FIG. 1 illustrates a configuration of an ultrasound diagnostic apparatus in external appearance, the ultrasound diagnostic apparatus including an ultrasonic transducer as an example of a MEMS transducer according to embodiments of the present invention. FIG. 2 is a block diagram illustrating an electrical configuration example of the ultrasound diagnostic apparatus according to the embodiments of the present invention.

Ultrasound diagnostic apparatus 1 is configured to include ultrasound-diagnostic-apparatus body 10, ultrasound probe 20, and cable 30.

Ultrasound probe 20 transmits ultrasonic signals to a human body as a subject (not illustrated), and receives the ultrasonic signals reflected by the human body. In ultrasound probe 20, multiple pMUT cells (described hereinbelow) that are ultrasonic transducers are arranged.

Ultrasound-diagnostic-apparatus body 10 is connected to ultrasound probe 20 via cable 30, and transmits transmission signals that are electrical signals via cable 30, so as to allow ultrasound probe 20 to transmit the ultrasonic signals. Additionally, ultrasound-diagnostic-apparatus body 10 forms ultrasonographic images of the internal state of the human body using electrical signals generated at ultrasound probe 20 based on the ultrasonic signals received by ultrasound probe 20.

Specifically, ultrasound-diagnostic-apparatus body 10 is configured to include operation input section 11, transmission section 12, reception section 13, image processing section 14, display section 15, and control section 16.

For example, a command indicating the start of diagnosis, information on a subject, or the like are input using operation input section 11. Operation input section 11 is an operation panel, a keyboard, or the like provided with multiple input switches, for example.

Transmission section 12 transmits control signals received from control section 16 to ultrasound probe 20 via cable 30. That is, transmission section 12 makes ultrasound probe 20 operate for transmission of ultrasonic signals to the subject.

Reception section 13 receives via cable 30, reception signals transmitted from ultrasound probe 20. That is, reception section 13 makes ultrasound probe 20 operate to receive ultrasonic signals coming from the subject in response to the transmitted ultrasonic signals. Then, reception section 13 outputs the received ultrasonic signals to image processing section 14.

Image processing section 14 uses the ultrasonic signals received from reception section 13 to generate an image (ultrasonographic image) for ultrasonic diagnosis in accordance with instructions by control section 16. The ultrasonographic image shows the internal state of the subject.

Display section 15 displays the ultrasonographic image generated by image processing section 14 in accordance with instructions by control section 16.

Control section 16 controls operation input section 11, transmission section 12, reception section 13, image processing section 14, and display section 15 according to their functions, so as to entirely control ultrasound diagnostic apparatus 1.

[Ultrasound Probe]

Figure 3:
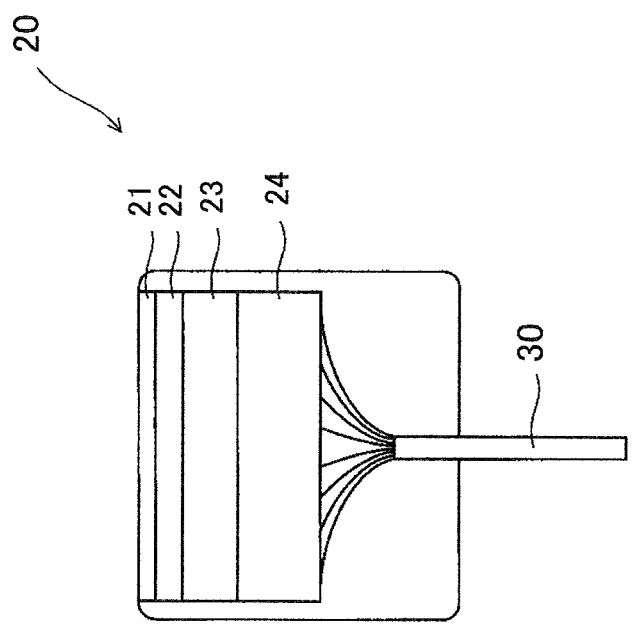
FIG. 3 is an explanatory view for explaining a configuration of an ultrasound probe.

FIG. 3 is an explanatory view for explaining a configuration of ultrasound probe 20. Ultrasound probe 20 includes protective layer 21, pMUT element 22 as an ultrasonic transmission/reception transducer, backing material 23, and signal processing circuit 24. Note that the detailed descriptions of pMUT element 22 will be given below.

Protective layer 21 protects pMUT element 22. This protective layer 21 is formed from a comparatively flexible material such as silicone rubber or the like which, when coming into contact with a human body, does not give discomfort to the human body, and which has an acoustic impedance comparatively similar to that of the human body.

Backing material 23 forms through-wiring for attenuating unnecessary vibration arising at pMUT element 22 and for electrically connecting pMUT element 22 to signal processing circuit 24. Additionally, backing material 23 has a function of transferring and diffusing, via signal processing circuit 24 through cable 30, heat arising at pMUT element 22, so as to prevent a temperature rise at the surface of the human body with which protective layer 21 comes into contact. Signal processing circuit 24 is a circuit which generates pulse signals for ultrasonic transmission, processes received pulse signals, and the like, and which is connected to ultrasound-diagnostic-apparatus body 10 via cable 30.

[pMUT Element]

Figure 4:
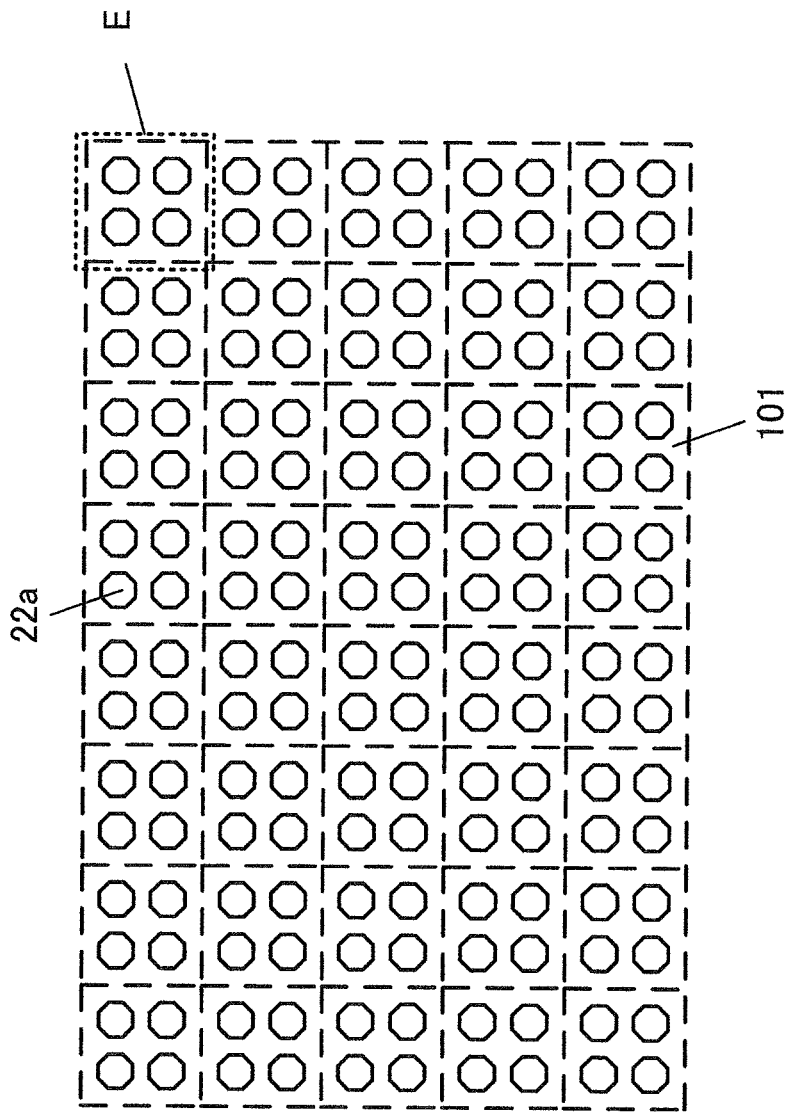
FIG. 4 is a plan view of a substrate for explaining diaphragms.

PMUT element 22 is produced using Micro Electro Mechanical Systems (MEMS) techniques. PMUT element 22 is formed by bonding together substrate 101 in which multiple diaphragms 22a as vibrators are disposed two-dimensionally (or, one-dimensionally) and substrate 401 (see FIG. 5 described below) in which signal detection circuit 400 configured to detect signals from diaphragms 22a is provided. FIG. 4 is a plan view of substrate 101 for explaining diaphragms 22a. Diaphragms 22a transmit/receive ultrasonic waves by vibration. In FIG. 4, the section surrounded by the dotted line (region E in FIG. 4) corresponds to one cell.

Figure 5:
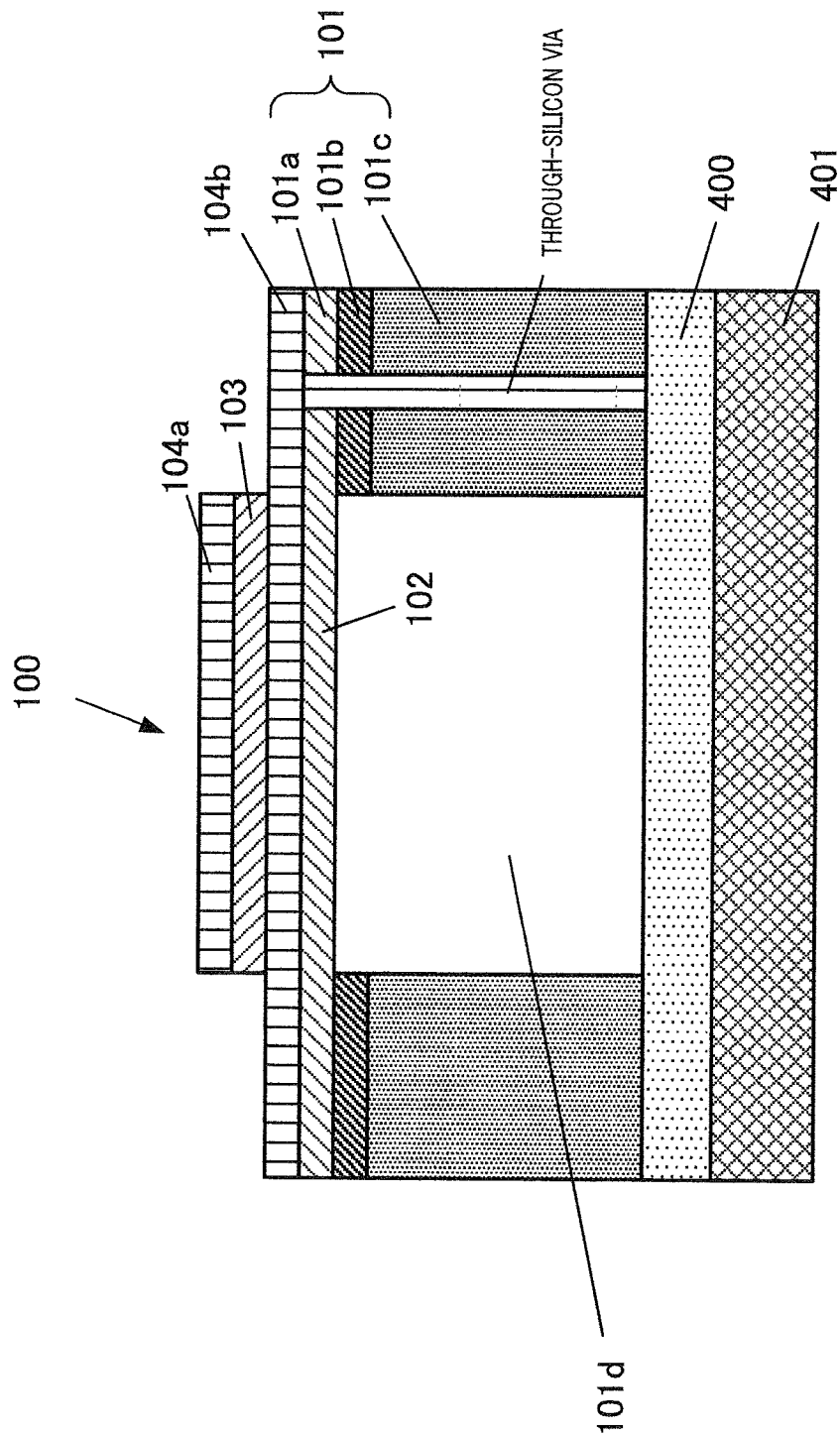
FIG. 5 is a sectional view of one of the diaphragms constituting a pMUT element.

FIG. 5 is a sectional view of one of diaphragms 22a constituting pMUT element 22. Diaphragm 22a is composed of piezoelectric element 100, and includes substrate 101 having opening 101d, vibrating plate 102, piezoelectric material layer 103, and electrodes 104a and 104b.

Substrate 101 is a Silicon on Insulator (SOI) substrate formed by stacking, for example, Si layer 101a, SiO$_2$ layer 101b, and Si layer 101c on one another. Substrate 101 is an example of the MEMS substrate of the present invention. Vibrating plate 102 is formed by opening 101d provided by removing Si layer 101c and SiO$_2$ layer 101b, for example, by etching from the undersurface side of substrate 101. That is, vibrating plate 102 has a thin plate structure formed by Si layer 101a and opening 101d.

Piezoelectric material layer 103 is composed of a thin film of PZT (lead zirconate titanate), for example, and is formed on the side opposite to opening 101d relative to vibrating plate 102 in order for vibrating plate 102 to be vibrated by an applied electric field. Piezoelectric material layer 103 is patterned and, for example, has a substantially regular octagonal cell shape in cross section. Note that, the cross section of piezoelectric material layer 103 may also have a shape other than regular octagonal (e.g., a circular shape, polygonal shape other than regular octagonal, or the like).

Electrode 104a is an electrode on the side of upper surface of piezoelectric material layer 103, and is a common electrode. In contrast, electrode 104b is an electrode on the side of undersurface of piezoelectric material layer 103, and is drawn out downward from substrate 101 via a through-silicon via or the like.

Drawn-out electrode 104b is electrically connected to signal detection circuit 400 disposed on substrate 401. Signal detection circuit 400 is a CMOS circuit for detecting signals from diaphragms 22a, for example. Substrate 401 is an example of an electronic circuit substrate of the present invention. Signal detection circuit 400 is electrically connected to signal processing circuit 24.

Diaphragms 22a are each designed such that the effectual acoustic impedance is consistent with the acoustic impedance of the living body, and thus can convey an ultrasonic wave to a living body efficiently. Specifically, the rigidity of each of diaphragms 22a may be optimized, and more preferably, the material and thickness of vibrating plate 102, the thickness of piezoelectric material layer 103, the diameter of diaphragm 22a, the space between electrodes 104a and 104b, and/or the like may be optimized appropriately depending on a resonance frequency, transmission characteristics (sensitivity, frequency band), reception characteristics (sensitivity, frequency band), and/or the like.

[Method for Producing pMUT Element 22]

Next, the method for producing pMUT element 22 configured as described above will be described.

To begin with, a SOI wafer having the stack structure in which SiO$_2$ layer 101b is stacked between two Si layers 101a and 101c is prepared as substrate 101, and electrode 104b is formed on a platelike silicon member on one side of substrate 101 by depositing titanium, gold, platinum, and the like by sputtering or the like.

Piezoelectric material layer 103 is formed on electrode 104b by depositing PZT by sputtering process, sol-gel process, or the like. Additionally, electrode 104a is formed on piezoelectric material layer 103 by depositing gold, platinum, and the like by sputtering or the like.

Next, electrode 104a, piezoelectric material layer 103, and electrode 104b are shaped one after another by patterning such that electrode 104a, piezoelectric material layer 103, and electrode 104b each have substantially regular octagonal cell shapes. Additionally, openings 101d are each formed at a position corresponding to vibrating plate 102 in the platelike member by etching or the like from the surface of substrate 101 facing away from vibrating plate 102 and piezoelectric material layer 103. Each of these cell shapes corresponds to diaphragm 22a.

In this way, electrode 104a, piezoelectric material layer 103, electrode 104b, and the platelike silicon member that is a part of substrate 101 are stacked on one another, and multiple vibrating plates 102 uncovered on the undersurface side of the stack are formed.

Then, electrode 104b on the lower side of piezoelectric material layer 103 is drawn out by the through-silicon via through substrate 101.

Substrate 101 in which multiple diaphragms 22a are formed as described above is bonded to substrate 401 on which signal detection circuit (CMOS circuit) 400 is formed in advance after substrate 101 is aligned to substrate 400. As for the bonding method, flip chip assembly techniques, such as an anisotropic conductive film (ACF), solder bump, and/or the like may be used, for example. Both of the electrodes are connected to signal detection circuit 400 at this time. The details of the alignment method will be described below.

As described above, diaphragms 22a of pMUT element 22 are produced by forming piezoelectric material layer 103 on one surface of substrate 101 that is a SOI substrate and thereafter by providing openings 101d in the other surface by etching to form vibrating plates 102.

It should be noted that, when multiple diaphragms 22a are formed in substrate 101 by the method as described above, an etching solution may flow comparatively more into places near the edge portion of the SOI wafer as substrate 101 than into a place near the central portion, so that the etching rate may increase in such places near the edge portion. In that case, variations in characteristics between those of diaphragms 22a formed near the central portion and those of diaphragms 22a formed near the edge portion of substrate 101 may arise.

The variations in characteristics of diaphragms 22a, when arise, make preferable transmission/reception of ultrasonic waves difficult. In order to avoid such a situation, some of produced multiple diaphragms 22a are determined as dummy diaphragms and are not used for the transmission/reception of ultrasonic waves in the embodiments of the present invention.

Figure 6:
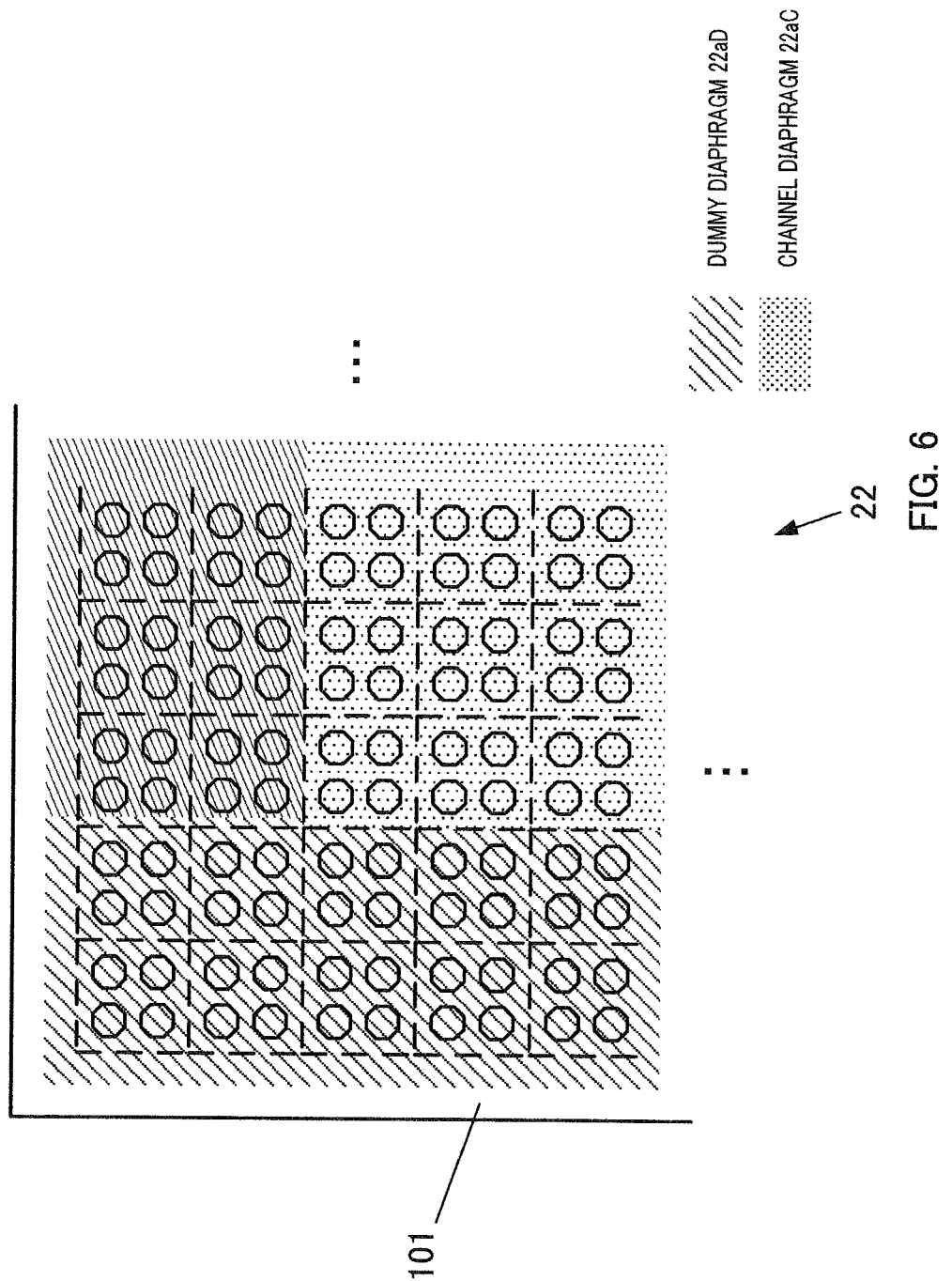
FIG. 6 is an explanatory view for explaining channel diaphragms constituting a channel for transmission/reception of ultrasonic waves, and for explaining dummy diaphragms.

FIG. 6 is an explanatory view for explaining channel diaphragms 22aC constituting a channel for transmission/reception of ultrasonic waves, and for explaining dummy diaphragms 22aD. In the example illustrated in FIG. 6, those of two-dimensionally disposed diaphragms 22a disposed in predetermined numbers of columns and rows (two columns and two rows in FIG. 6) from the farthest edge portion are determined as dummy diaphragms 22aD, and those of two-dimensionally disposed diaphragms 22a disposed inside dummy diaphragms 22aD are determined as channel diaphragms 22aC. Note that the solid line corresponds to the edge of substrate 101 in FIG. 6.

There is no difference between methods for producing channel diaphragms 22aC and dummy diaphragms 22aD, and their structures are the same at the design stage. In the example illustrated in FIG. 6, those of diaphragms 22a which are disposed at the position where the variations in characteristics arise at the production stage (during etching), for example, at the position near the edge portion are dummy diaphragms 22aD. Dummy diaphragms 22aD are not used for transmission/reception of ultrasonic waves, and are not connected to signal detection circuit 400. Specifically, dummy diaphragms 22aD may be configured not to include the aforementioned through-silicon vias from electrodes 104b, for example.

In this way, some of multiple diaphragms 22a produced by the same production method are determined as dummy diaphragms 22aD which are not used for transmission/reception of ultrasonic waves, so that the characteristics of pMUT element 22 as the ultrasonic transmission/reception transducer can be made preferable. Note that, although those of diaphragms 22a formed near the edge portion are determined as dummy diaphragms 22aD in the example illustrated in FIG. 6, the present invention is not limited to this example and those of diaphragms 22a disposed at other positions may also be determined as dummy diaphragms 22aD.

[Alignment Method]

Substrate 101 in which multiple diaphragms 22a are formed by the aforementioned production method is aligned to substrate 401 on which signal detection circuit 400 is formed, and thereafter substrates 101 and 401 are bonded to each other. Hereinbelow, the method for aligning substrate 101 to substrate 401 will be described.

<Method 1>

Figure 7A:
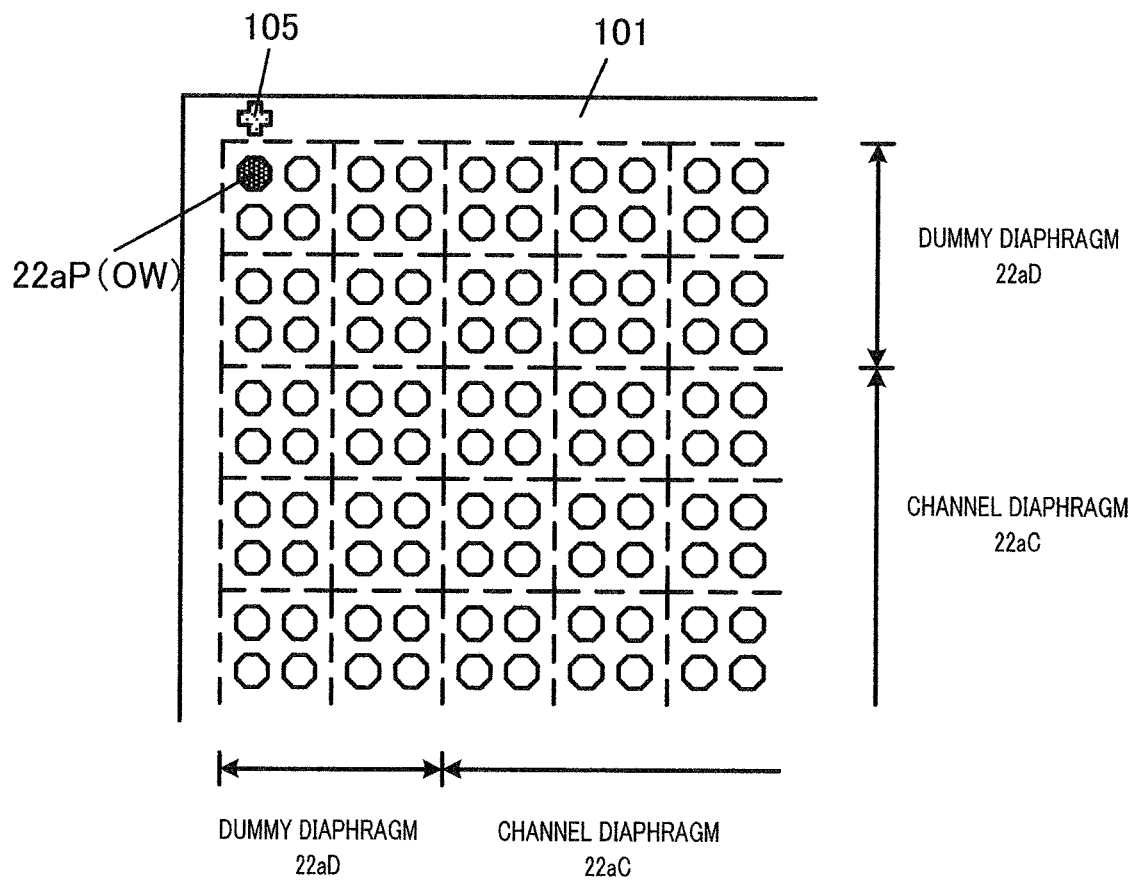
FIG. 7A is an explanatory view for explaining an alignment diaphragm.
Figure 7B:
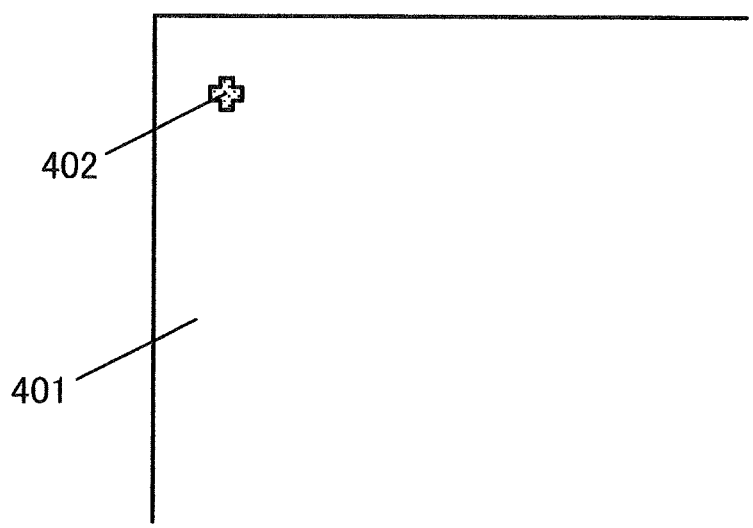
FIG. 7B is a plan view of the substrate for explaining an alignment mark.

FIG. 7A is an explanatory view for explaining an alignment diaphragm, and FIG. 7B is a plan view of substrate 401 for explaining alignment mark 402. In FIG. 7B, illustration of signal detection circuit 400 formed on substrate 401 is omitted.

As illustrated in FIG. 7A, at least one of multiple dummy diaphragms 22aD is used for alignment. Hereinbelow, dummy diaphragm 22aD used for alignment is referred to as "alignment diaphragm 22aP." Note that, as in the illustration of FIG. 6, FIG. 7A illustrates the case where those of diaphragms 22a which are disposed in predetermined columns and rows near the edge portion of substrate 101 are determined as dummy diaphragms 22aD.

In Method 1, vibrating plate 102, piezoelectric material layer 103, and electrodes 104a and 104b constituting alignment diaphragm 22aP are broken up and removed, and observation window OW is created. This breaking-up and removal are carried out, for example, immediately before substrate 101 and substrate 401 are aligned to each other. Breaking-up and removal of alignment diaphragm 22aP may be carried out by breaking up and removing vibrating plate 102, piezoelectric material layer 103, and electrodes 104a and 104b constituting alignment diaphragm 22aP, for example, using a stick or the like having a diameter smaller than that of dummy diaphragm 22aD. That is, in Method 1, observation window OW is a mere hole having the same size and shape as other diaphragms 22a. Note that, vibrating plate 102, piezoelectric material layer 103, and electrodes 104a and 104b are each a thin film having a thickness of the order of μm, and therefore, breaking-up of alignment diaphragm 22aP can be easily done only by lightly touching with the aforementioned stick or the like.

As illustrated in FIG. 7B, alignment mark 402 is provided at a position of substrate 401 corresponding to observation window OW of substrate 101. Alignment mark 402 is an example of an alignment item of the present invention.

Moreover, as illustrated in FIG. 7A, alignment mark 105 of the same shape and of the same direction as alignment mark 402 provided on substrate 401 illustrated in FIG. 7B is provided on substrate 101 in advance. Note that examples of methods for forming alignment marks 105 and 402 include a sputtering process, vapor deposition process, pattern printing process, and the like.

Figure 8:
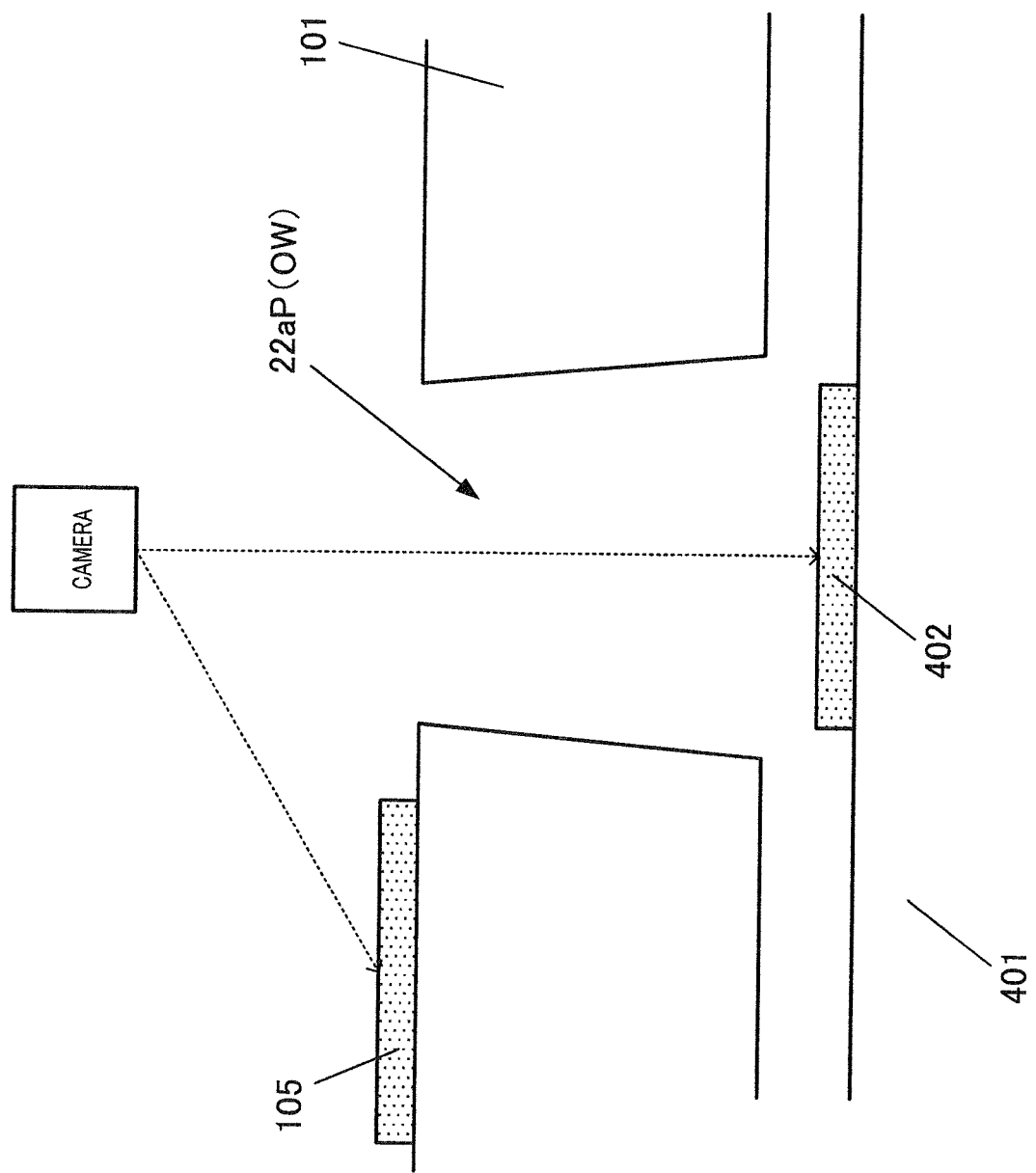
FIG. 8 is an explanatory view for explaining alignment method 1.

The alignment and bonding of substrates 101 and 401 configured as described above are carried out, for example, using an optical recognition device (not illustrated) or the like. Specifically, as illustrated in FIG. 8, while substrate 101 is held above substrate 401, substrate 101 or substrate 401 is moved to a position where alignment mark 402 provided on substrate 401 is preferably observed by a camera of the optical recognition device through observation window OW. FIG. 8 is an explanatory view for explaining alignment method 1 and is a sectional view of substrates 101 and 401 at the position of alignment diaphragm 22aP. Note that, illustration of diaphragms 22a other than alignment diaphragm 22aP is omitted in FIG. 8 for explanation.

Here, the optical recognition device moves substrate 101 or substrate 401 until the shape and direction of alignment mark 402 recognized through observation window OW and the shape and direction of alignment mark 105 provided on substrate 101 correspond to each other in pattern matching. This allows accurate alignment between substrates 101 and 401.

Note that, although the number and positions of observation windows OW and alignment marks 402 are not particularly limited in the embodiments of the present invention, it is desirable to provide at least two or more observation windows OW and alignment marks 402 on each of substrates 101 and 401 from a viewpoint of alignment between substrates. More preferably, it is desirable to provide observation windows OW and alignment marks 402 at positions of each of substrates 101 and 401 corresponding to dummy diaphragms 22aD existing on opposite sides of the edge portion of substrate 101 across the center of substrate 101. Still more preferably, observation windows OW and alignment marks 402 may also be provided at positions corresponding to four dummy diaphragms 22aD existing on two mutually perpendicular lines among multiple lines passing through the center.

<Method 2>

Although alignment mark 105 used for pattern matching is provided on substrate 101 in aforementioned Method 1, Method 2 described below will be described in relation to the case where alignment mark 105 is not provided on substrate 101.

To begin with, substrates 101 and 401 for which the alignment is accomplished are prepared, and the shape of alignment mark 402 recognized through observation window OW in the case where substrates 101 and 401 are successfully aligned to each other (such a shape may hereinafter be referred to as "first shape") is stored in advance in the optical recognition device. Then, when substrates 101 and 401 are actually aligned to each other, the optical recognition device moves substrate 101 or substrate 401 until the shape of alignment mark 402 recognized through observation window OW corresponds to the first shape stored in advance. This allows accurate alignment between substrates 101 and 401.

Note that, not only the shape of alignment mark 402 but also the shape of inner wall surface of observation window OW and the shape of alignment mark 402 recognized through observation window OW may also be stored together in the optical recognition device in advance as the aforementioned first shape.

<Method 3>

Figure 9:
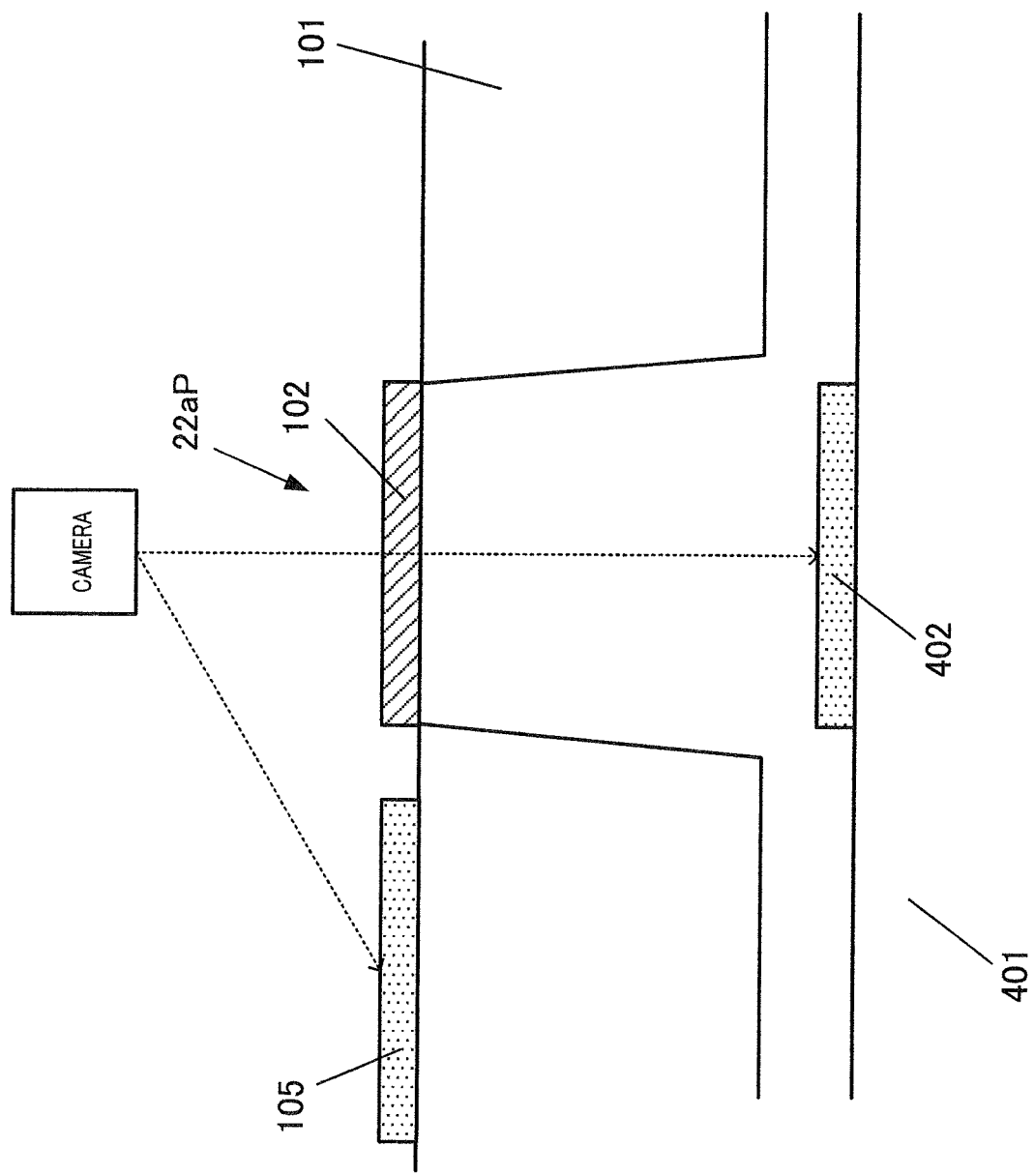
FIG. 9 is an explanatory view for explaining alignment method 3 in which infrared light is used.

As described above, vibrating plate 102 that is one component element of diaphragm 22a has the thin plate structure composed of the Si layer. It has been understood that silicon thin films transmit infrared radiation. The optical recognition device can use the infrared radiation for recognition of alignment mark 402 so as to perform alignment without breaking up alignment diaphragm 22aP. FIG. 9 is an explanatory view for explaining alignment method 3 in which infrared light is used.

However, because piezoelectric material layer 103 and electrodes 104a and 104b prevent transmission of infrared radiation, it is desirable to remove piezoelectric material layer 103 and electrodes 104a and 104b by etching or the like before the alignment process.

<Method 4>

Method 4 is a method in which scribe lines used during chip separation are utilized. Substrate 101 that is a SOI substrate includes predetermined scribe lines. In Method 4, alignment diaphragm 22aP is provided on any of these scribe lines.

FIG. 10 is an explanatory view for explaining a case where alignment diaphragm 22aP is provided on one of scribe lines SL.

In the case where alignment diaphragm 22aP is provided on one of scribe lines SL, observation window OW is created as with Method 1 by removing a remainder of alignment diaphragm 22aP, and the optical recognition device recognizes the shape of alignment mark 402 on substrate 401 through observation window OW, so that alignment may be performed by pattern matching with alignment mark 105 provided on substrate 101. Additionally or alternatively, the alignment may also be performed based on the shape of side wall surface left after removal of alignment diaphragm 22aP (the shape of side wall surface of observation window OW) and based on the shape of alignment mark 402 recognized through observation window OW. Additionally or alternatively, the alignment may also be performed by providing an alignment mark in the side surface of substrate 101 during scribing and by using the alignment mark.

<Function and Effect>

As described above, in the method for producing a MEMS transducer according to the embodiments of the present invention, substrate 101 (corresponding to the MEMS substrate of the present invention) is produced by using MEMS technique to form multiple diaphragms 22a in a substrate by forming piezoelectric material layer 103 on one surface of the substrate and thereafter by forming openings 101d in the substrate from the other surface of the substrate; substrate 101 and substrate 401 on which signal detection circuit 400 is formed (substrate 401 corresponds to the electronic circuit substrate of the present invention) are aligned to each other by using at least one of multiple diaphragms 22a as alignment diaphragm 22aP; and substrate 101 and substrate 401 are bonded together.

In this way, according to the method for producing the MEMS transducer according to the embodiments of the present invention, substrate 101 is aligned to substrate 401 by using a part of multiple diaphragms 22a formed on substrate 101 as alignment diaphragm 22aP. This allows highly accurate alignment using a common optical recognition device or the like neither without an additional process nor without highly accurate equipment for alignment. Additionally, a structure for alignment (alignment diaphragm 22aP) is provided not on the side of substrate 401 that is the electronic circuit substrate side but on the side of substrate 101 that is the MEMS substrate side, so that it is preferable in view of the cost that the same circuit can be used as the electronic circuit substrate when the MEMS transducer in which the MEMS substrate including various characteristics and the electronic circuit substrate are bonded together is produced. From the above reasoning, substrate 101 that is the MEMS substrate and substrate 401 that is the electronic circuit substrate can be connected to each other with high accuracy and to low cost.

Note that alignment using the method for producing a MEMS transducer according to the embodiments of the present invention brings about the following advantages. When each of diaphragms 22a is formed in substrate 101, upper and lower electrodes (electrodes 104a and 104b) and piezoelectric substance material layer 103 can be processed from the front surface using the alignment mark existing on the same front surface. In contrast, when opening 101d is formed, it is necessary to perform backside alignment from the back surface based on the alignment mark on the front surface and to process from the back surface, so that the position of piezoelectric material layer 103 may be shifted slightly from the position of opening 101d depending on the accuracy. With the use of the method for producing of a MEMS transducer according to the embodiments of the present invention, it is made possible to perform alignment regardless of the position of piezoelectric material layer 103 even when the position of piezoelectric material layer 103 is shifted slightly from the position of opening 101d since the alignment is performed based on the shape of alignment mark 402 recognized through observation window OW.

Additionally, in the method for producing of a MEMS transducer according to the embodiments of the present invention, multiple diaphragms 22a include channel diaphragms 22aC which constitute the channel used for transmission/reception of ultrasonic waves (channel diaphragms 22aC correspond to the first diaphragms of the present invention) and dummy diaphragms 22aD not used for transmission/reception of ultrasonic waves (dummy diaphragms 22aD correspond to the second diaphragms of the present invention), and alignment diaphragm 22aP is at least one of dummy diaphragms 22aD.

With such a configuration, alignment diaphragm 22aP can be formed simultaneously in the same processing process as the normal channel diaphragms 22aC, so that high relative-position accuracy can be ensured and the cost can be held down.

Additionally, in the method for producing of a MEMS transducer according to the embodiments of the present invention, observation window OW is further created by destroying and removing alignment diaphragm 22aP, and, when substrates 101 and 401 are aligned to each other, substrates 101 and 401 are aligned to each other based on observation window OW and alignment mark 402 provided on substrate 401 in advance (alignment mark 402 corresponds to the alignment item of the present invention).

Alternatively, in the method for producing of a MEMS transducer according to the embodiments of the present invention, piezoelectric material layer 103 located on alignment diaphragm 22aP is further removed, and, when substrates 101 and 401 are bonded together, substrates 101 and 401 are aligned to each other based on alignment diaphragm 22aP and alignment mark 402 provided on substrate 401 in advance, using infrared radiation that passes through alignment diaphragm 22aP from which piezoelectric material layer 103 is removed.

Alternatively, in the method for producing of a MEMS transducer according to the embodiments of the present invention, alignment diaphragm 22aP is further formed on scribe line SL used for singulation of substrate 101 when substrate 101 is produced, and, when substrates 101 and 401 are bonded together, substrates 101 and 401 are aligned to each other based on alignment diaphragm 22aP and alignment mark 402 provided on substrate 401 in advance.

Such configurations allow highly accurate alignment using a common optical recognition device or the like neither without an additional process nor without highly accurate equipment for alignment. Therefore, substrate 101 that is the MEMS substrate and substrate 401 that is the electronic circuit substrate can be connected to each other with high accuracy and to low cost.

<Modification>

Although the embodiments of the present invention have been described above with reference to the drawings, the present invention is not limited to these examples. The technical scope of the present invention encompasses various variations and modifications which a person skilled in the art can conceive within the scope of the appended claims. Moreover, any combination of features of the above-mentioned embodiments may be made without departing from the spirit of the disclosure.

In the above-described embodiments, the pMUT that is an ultrasonic transducer has been described as an example of the MEMS transducer. However, the present invention is not limited to this example. For example, the present invention is widely applicable to various kinds of piezoelectric modules (and piezoelectric devices using the piezoelectric modules), each of which includes a diaphragm layer and a piezoelectric material layer disposed on the diaphragm layer and utilizes converting function of converting mechanical deformation of a piezoelectric substance to voltage. Specifically, the present invention may also be applied, for example, to an angular velocity sensor, an inkjet head, a minute-mirrors actuating element, or the like.

INDUSTRIAL APPLICABILITY

The present invention is suitable for a method for producing a MEMS transducer used for an ultrasound diagnostic apparatus.

Although embodiments of the present invention have been described and illustrated in detail, it is clearly understood that the same is by way of illustration and example only and not limitation, the scope of the present invention should be interpreted by terms of the appended claims.

What is claimed is:

1. A method for producing a MEMS transducer, the method comprising:
  producing a MEMS substrate to form a plurality of diaphragms in a substrate, the plurality of diaphragms being formed by forming a piezoelectric material layer on one surface of the substrate and thereafter by forming openings in the substrate from an other surface of the substrate;
  performing alignment between the MEMS substrate and an electronic circuit substrate by using at least one of the plurality of diaphragms as an alignment diaphragm; and
  bonding together the MEMS substrate and the electronic circuit substrate;
  creating an observation window by destroying and removing the alignment diaphragm, wherein, when performing the alignment between the MEMS substrate and the electronic circuit substrate, the alignment is performed based on the observation window and an alignment item provided in advance on the electronic circuit substrate.

2. The method for producing the MEMS transducer according to claim 1, wherein the MEMS transducer is a piezoelectric micromachined ultrasonic transducer (pMUT).

3. The method for producing the MEMS transducer according to claim 1, wherein a signal detection circuit is formed on the electronic circuit substrate, the signal detection circuit detecting a transmission signal or a reception signal for transmission or reception of an ultrasonic wave at the plurality of diaphragms.

4. The method for producing the MEMS transducer according to claim 1, wherein
  the plurality of diaphragms include first diaphragms constituting a channel used for the transmission or reception of the ultrasonic wave and second diaphragms not used for the transmission or reception of the ultrasonic wave, and
  the alignment diaphragm is at least one of the second diaphragms.

5. A method for producing a MEMS transducer, the method comprising:
  producing a MEMS substrate to form a plurality of diaphragms in a substrate, the plurality of diaphragms being formed by forming a piezoelectric material layer on one surface of the substrate and thereafter by forming openings in the substrate from another surface of the substrate;
  performing alignment between the MEMS substrate and an electronic circuit substrate by using at least one of the plurality of diaphragms as an alignment diaphragm; and
  bonding together the MEMS substrate and the electronic circuit substrate;
  removing the piezoelectric material layer located on the alignment diaphragm, wherein, when bonding together the MEMS substrate and the electronic circuit substrate, the alignment is performed by using infrared radiation that passes through the alignment diaphragm from which the piezoelectric material layer is removed, the alignment being performed based on the alignment diaphragm and an alignment item provided in advance on the electronic circuit substrate.

6. A method for producing a MEMS transducer, the method comprising:
  producing a MEMS substrate to form a plurality of diaphragms in a substrate, the plurality of diaphragms being formed by forming a piezoelectric material layer on one surface of the substrate and thereafter by forming openings in the substrate from another surface of the substrate;
  performing alignment between the MEMS substrate and an electronic circuit substrate by using at least one of the plurality of diaphragms as an alignment diaphragm; and
  bonding together the MEMS substrate and the electronic circuit substrate;
  forming the alignment diaphragm on a scribe line used for singulation of the MEMS substrate, when producing the MEMS substrate, wherein, when bonding together the MEMS substrate and the electronic circuit substrate, the alignment is performed based on the alignment diaphragm and an alignment item provided in advance on the electronic circuit substrate.

* * * * *